United States Patent [19]

[11] Patent Number: 4,505,931

[45] Date of Patent: Mar. 19, 1985

Ehrenfreund

[54] PESTICIDAL N-(4-ALKENYLTHIO)-PHENYL-N'-BENZOYLUREAS

[75] Inventor: Josef Ehrenfreund, Allschwil, Switzerland

[73] Assignee: Ciba-Geigy Corporation, Ardsley, N.Y.

[21] Appl. No.: 114,934

[22] Filed: Jan. 24, 1980

[30] Foreign Application Priority Data

Feb. 1, 1979 [CH] Switzerland .......................... 983/79
Oct. 15, 1979 [CH] Switzerland .......................... 9261/79

[51] Int. Cl.[3] .................... A01N 47/28; C07C 127/22
[52] U.S. Cl. .................................... 514/594; 564/44
[58] Field of Search .................... 424/322; 260/553 E; 564/44

[56] References Cited

U.S. PATENT DOCUMENTS

| | | | |
|---|---|---|---|
| 3,989,842 | 11/1976 | Wellinga et al. | 260/553 E |
| 4,005,223 | 1/1977 | Sirrenberg et al. | 424/322 |
| 4,085,226 | 4/1978 | Sirrenberg et al. | 424/322 |
| 4,089,975 | 5/1978 | Wade et al. | 424/322 |
| 4,139,636 | 2/1979 | Sirrenberg et al. | 424/322 |
| 4,162,330 | 7/1979 | Ehrenfreund | 424/322 |
| 4,170,657 | 10/1979 | Rigterink | 424/322 |

FOREIGN PATENT DOCUMENTS

| | | |
|---|---|---|
| 832304 | 2/1976 | Belgium . |
| 844066 | 7/1976 | Belgium . |
| 843906 | 1/1977 | Belgium . |
| 2123236 | 12/1971 | Fed. Rep. of Germany . |
| 2601780 | 1/1976 | Fed. Rep. of Germany . |
| 2504982 | 8/1976 | Fed. Rep. of Germany . |
| 2537413 | 3/1977 | Fed. Rep. of Germany . |
| 2726684 | 1/1979 | Fed. Rep. of Germany . |
| 1324293 | 7/1973 | United Kingdom . |
| 1460410 | 1/1977 | United Kingdom . |
| 1488644 | 10/1977 | United Kingdom . |
| 1492365 | 11/1977 | United Kingdom . |
| 1492364 | 11/1977 | United Kingdom . |

OTHER PUBLICATIONS

Wellinga et al., J. Aug. Food Chem., 21(3), 348,(1973).

*Primary Examiner*—Allen J. Robinson
*Attorney, Agent, or Firm*—Frederick H. Rabin; Bruce M. Collins; John P. Spitals

[57] ABSTRACT

Novel N-(4-alkenylthio)-phenyl-N'-benzoylureas of the formula

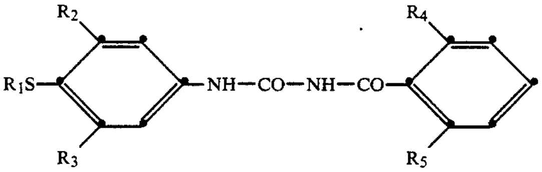

wherein $R_1$ is a $C_3$-alkenyl group, or a $C_3$-alkenyl group which is mono- or disubstituted with chlorine or bromine, $R_2$ and $R_3$ independently of one another are each hydrogen or chlorine, $R_4$ is hydrogen, fluorine or chlorine, and $R_5$ is fluorine or chlorine; processes for producing these compounds, and also compositions containing the compounds, for use in combating pests, particularly in combating insect pests in the field of plant protection, and combating ectoparasites. The compounds have high ovicidal activity.

5 Claims, No Drawings

PESTICIDAL N-(4-ALKENYLTHIO)-PHENYL-N'-BENZOYLUREAS

The present invention relates to novel substituted N-(4-alkenylthio)-phenyl-N'-benzoylureas, to processes for producing them, and to their use in combating pests.

The substituted N-(4-alkenylthio)-phenyl-N'-benzoylureas according to the invention have the formula

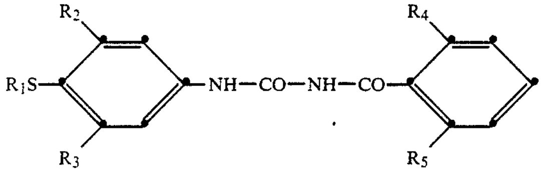

(I)

wherein $R_1$ is a $C_3$-alkenyl group, or a $C_3$-alkenyl group which is mono- or disubstituted with chlorine or bromine;

$R_2$ and $R_3$ independently of one another are each hydrogen or chlorine;

$R_4$ is hydrogen, fluorine or chlorine; and $R_5$ is fluorine or chlorine.

Compounds of the formula I according to the invention which are preferred by virtue of their action as pesticidal active substances are those wherein $R_1$ is the radical $$-CH_2-CH=CH-R_6$$

wherein $R_6$ is hydrogen, chlorine or bromine, preferably chlorine or bromine.

Of particular interest also are compounds of the formula I wherein $R_2$ and $R_3$ are each chlorine.

Furthermore, preferred compounds of the formula I are those wherein $R_3$ is hydrogen, and those compounds wherein at least one of the radicals $R_4$ and $R_5$ is fluorine.

The compounds of the formula I occur where possible as cis/trans isomeric mixtures. Thus, the term 'compounds of the formula I' is to be understood as embracing both the cis or trans forms and the corresponding isomeric mixtures. An isomeric mixture can be separated, for example by means of known chromatographical methods of separation and subsequent elution, into the isomeric forms. For synthesis of stereochemically homogeneous compounds of the formula I, there are advantageously used stereochemically homogeneous starting compounds of the following formula II or IV.

The compounds of the formula I can be produced by processes known per se (see, inter alia, the German Offenlegungsschriften Nos. 2,123,236 and 2,601,780).

A compound of the formula I can thus be obtained for example by reacting (a) a compound of the formula II

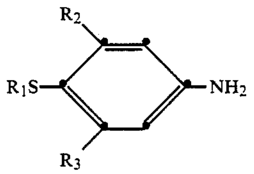

(II)

with a compound of the formula III

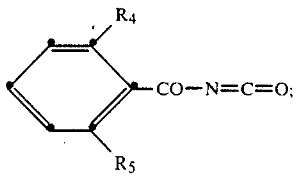

(III)

or (b) a compound of the formula IV

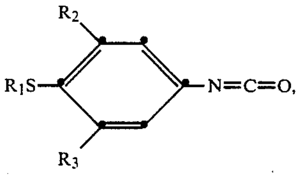

(IV)

optionally in the presence of a basic substance, with a compound of the formula V

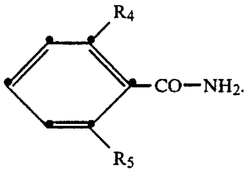

(V)

In the above formulae II, III, IV and V, the radicals $R_1$, $R_2$, $R_3$, $R_4$ and $R_5$ have the meanings given under the formula I.

The processes (a) and (b) mentioned are preferably performed under normal pressure and in the presence of an organic solvent or diluent. Suitable solvents or diluents are for example: ethers and ethereal compounds, such as diethyl ether, dipropyl ether, dibutyl ether, dioxane, dimethoxyethane and tetrahydrofuran; N,N-dialkylated carboxylic acid amides; aliphatic, aromatic as well as halogenated hydrocarbons, particularly benzene, toluene, xylene, chloroform, methylene chloride, carbon tetrachloride and chlorobenzene; nitriles such as acetonitrile or propionitrile; dimethylsulfoxide, and also ketones, for example acetone, methyl ethyl ketone, methylisopropyl ketone and methylisobutyl ketone. Process (a) is in general performed a a temperature of −10° to 100° C., preferably between 15° and 25° C., optionally in the presence of an organic base, for example triethylamine. Process (b) is performed at a temperature of 0° to 150° C., preferably at the boiling point of the employed solvent, and optionally in the presence of an organic base, such as pyridine, and/or with the addition of an alkali metal salt or alkaline-earth metal salt, preferably sodium.

The starting materials of the formulae II, III, IV and V are known, or they can be produced by processes analogous to known processes (see, for example, British Patent Specification No. 1141183, and German Offenlegungsschrift No. 1,193,047).

It is already known that certain substituted N-phenyl-N'-benzoylureas have insecticidal properties (see German Offenlegungsshriften Nos. 2,123,236, 2,504,982, 2,531,279, 2,537,413 and 2,726,684, and also the Belgian Patent Specification Nos. 832,304, 843,906 and 844,066). In the U.S. Pat. No. 4,089,975 and the German Offenlegungsschrift No. 2,601,780 are described N-alkylthiophenyl-N'-benzoylureas and N-haloalkylthiophenyl-N'-benzoylureas, respectively, and their use as insecticides. Compounds of similar structure are known also from J. Agr. Food Chemistry, Vol. 21, (3) 348 (1973). These known compounds have only relatively low insecticidal activity.

It has now been found that in contrast the N-alkenylthiophenyl-N'-benzoylureas of the formula I according to the invention, whilst having high tolerance to plants and negligible toxicity to warm-blooded animals, surprisingly have excellent activity as pesticidal active substances. They are suitable in particular for combating pests which infest plants and animals.

The compounds of the formula I are especially suitable for combating insects of the orders: Lepidoptera, Coleoptera, Homoptera, Heteroptera, Diptera, Thysanoptera, Orthoptera, Anoplura, Siphonaptera, Mallophage, Thysanua, Isoptera, Psocoptera and Hymenoptera.

In addition to having a favourable action against flies, such as Musca domestica, and against mosquito larvae, the compounds of the formula I can also be used for combating insects which damage plants by eating, in crops of ornamental plants and useful plants, especially in cotton crops (for example against Spodoptera littoralis and Heliothis virescens), and also in crops of fruit and of vegetables (for example against Leptinotarsa decemlineata, Laspeyresia pomonella and Epilachna varivestis). The compounds of the formula I are characterised by a high larvicidal activity and, in particular, a very good ovicidal activity. When compounds of the formula I are taken with the feed by adult insects, there can be observed in many cases, especially with Coleoptera, for example Anthonomus grandis, a reduced oviposition and/or a reduced hatching rate.

The compounds of the formula I are moreover suitable for combating ectoparasites in domestic animals and in productive animals, for example by treatment of animals, livestock housing and pasture land.

The action of the compounds according to the invention or of compositions containing them can be considerably widened and adapted to suit prevailing conditions by the addition of other insecticides. Suitable additives are for example the following active substances: organic phosphorus compounds, nitrophenols and derivatives thereof, formamidines, ureas, carbamates and chlorinated hydrocarbons.

The compounds of the formula I can be combined with particular advantage also with substances which have a pesticidally intensifying effect. Examples of such compounds are, inter alia: piperonylbutoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioates.

The compounds of the formula I can be used on their own or together with suitable carriers and/or additives. Suitable carriers and additives may be solid or liquid and correspond to the substances common in formulation practice, such as natural or regenerated substances, solvents, dispersing agents, wetting agents, adhesives, thickeners, binders and/or fertilisers. For application, the compounds of the formula I can be processed into the form of dusts, emulsion concentrates, granulates, dispersions, sprays, solutions or suspensions, the formulation of these preparations being effected in a manner commonly known in the art. Also to be mentioned are cattle dips and spray races, in which aqueous preparations are used. These forms of preparation are particularly suitable for combating zooparasitic pests.

The compositions according to the invention are produced in a manner known per se by the intimate mixing and/or grinding of active substances of the formula I with suitable carriers, optionally with the addition of dispersing agents or solvents which are inert to the active substances. The active substances can be obtained and used in the following forms:

solid preparations: dusts, scattering agents or granulates (coated granules, impregnated granules and homogeneous granules);

liquid preparations:

(a) water-dispersible concentrates of active substance: wettable powders, pastes or emulsions;

(b) solutions.

The content of active substance in the described compositions is between 0.1 and 95%.

The active substances of the formula I can be formulated for example as follows:

Dusts

The following substances are used to produce (a) a 5% dust and (b) a 2% dust:

(a)

5 parts of active substance, and
95 parts of talcum;

(b)

2 parts of active substance,
1 part of highly dispersed silicic acid, and
97 parts of talcum.

The active substance is mixed and ground with the carriers.

Granulate

The following ingredients are used to produce a 5% granulate:

5 parts of active substance,
0.25 part of epoxidised vegetable oil,
0.25 part of cetyl polyglycol ether,
3.50 parts of polyethylene glycol, and
91 parts of kaolin (particle size 0.3–0.8 mm).

The active substance is mixed with epoxidised vegetable oil and dissolved in 6 parts of acetone, and the polyethylene glycol and cetyl polyglycol ether are then added. The solution obtained is sprayed onto kaolin and the acetone is subsequently evaporated off in vacuo.

Wettable powders

The following constituents are used to produce (a) a 40% wettable powder, (b) and (c) a 25% wettable powder, and (d) a 10% wettable powder:

(a)

40 parts of active substance,
5 parts of sodium lignin sulfonate,
1 part of sodium dibutyl-naphthalene sulfonate, and
54 parts of silicic acid;

(b)

25 parts of active substance,
4.5 parts of calcium lignin sulfonate,
1.9 parts of Champagne chalk/hydroxyethyl cellulose mixture (1:1),
1.5 parts of sodium dibutyl-naphthalene sulfonate,
19.5 parts of silicic acid,
19.5 parts of Champagne chalk, and
28.1 parts of kaolin;

(c)

25 parts of active substance, 2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselgur, and
46 parts of kaolin;

(d)
10 parts of active substance,
3 parts of a mixture of the sodium salts of saturated fatty alcohol sulfates,
5 parts of naphthalenesulfonic acid/fomaldehyde condensate, and
82 parts of kaolin.

The active substance is intimately mixed in suitable mixers with the additives, and the mixture is then ground in the appropriate mills and rollers to obtain wettable powders which can be diluted with water to give suspensions of the desired concentration.

Emulsifiable concentrates

The following substances are used to produce (a) a 10% emulsifiable concentrate, (b) a 25% emulsifiable concentrate and (c) a 50% emulsifiable concentrate:

(a)
10 parts of active substance,
3.4 parts of epoxidised vegetable oil,
3.4 parts of a combination emulsifier consisting of fatty alcohol polyglycol ether and alkylaryl sulfonate calcium salt,
40 parts of dimethylformamide, and
43.2 parts of xylene;

(b)
25 parts of active substance,
2.5 parts of epoxidised vegetable oil,
10 parts of an alkylarylsulfonate/fatty alcohol polyglycol ether mixture,
5 parts of dimethylformamide, and
57.5 parts of xylene;

(c)
50 parts of active substance,
4.2 parts of tributylphenol-polyglycol ether,
5.8 parts of calcium-dodecylbenzenesulfonate,
20 parts of cyclehexanone, and
20 parts of xylene.

Emulsions of the concentration required can be prepared from these concentrates by dilution with water.

Spray

The following constituents are used to produce (a) a 5% spray and (b) a 95% spray:

(a)
5 parts of active substance,
1 part of epoxidised vegetable oil,
94 parts of ligroin (boiling limits 160°–190° C.);

(b)
95 parts of active substance, and
5 parts of epoxidised vegetable oil.

EXAMPLE 1

5.8 g of 2,6-difluorobenzoylisocyanate is added, at room temperature and with the exclusion of moisture, to a solution of 4.95 g of 4-allylthioaniline in 25 ml of absolute ether. The precipitate formed after a short period of time is filtered off with suction and washed with ether. Recrystallisation from toluene yields N-(4-allylthio)-phenyl-N'-2,6-difluorobenzoylurea having a melting point of 164°–165° C.

The following compounds of the formula I are produced by procedures analogous to those described in the foregoing.

| $R_1$ | $R_2$ | $R_3$ | $R_4$ | $R_5$ | Melting point [°C.] |
|---|---|---|---|---|---|
| $-CH_2-CH=CHCl$ | H | H | F | F | 139–140* |
| $-\underset{Cl}{\underset{\vert}{CH}}-CH=CH_2$ | H | H | F | F | |
| $-CH_2-CH=CH_2$ | H | H | F | F | 164–165 |
| $-CH_2-CH=CH_2$ | Cl | H | F | Cl | 168–170 |
| $-CH_2-CH=CH_2$ | Cl | H | H | Cl | 155–158 |
| $-CH_2-CH=CH_2$ | Cl | H | H | F | 149–151 |
| $-CH_2-CH=CH_2$ | Cl | H | Cl | Cl | 160–163 |
| $-CH_2-\underset{Br}{\underset{\vert}{C}}=CH_2$ | H | H | F | F | 172 |
| $-CH_2-\underset{Cl}{\underset{\vert}{C}}=CH_2$ | H | H | F | F | |
| $-CH_2-CH=CHCl$ | Cl | H | F | F | 145–164* |
| $-CH_2-CH=CHBr$ | H | H | F | F | 143–147* |
| $-CH_2-CH=CH_2$ | Cl | Cl | F | F | 146–150 |
| $-CH_2-CH=CHCl$ | Cl | Cl | F | F | 156–160* |
| $-CH_2-CH=CHBr$ | Cl | Cl | F | F | 144,5–146* |
| $-CH_2-CH=CHBr$ | H | H | H | Cl | 132–134* |
| $-CH_2-\underset{Br}{\underset{\vert}{C}}=CH_2$ | H | H | H | Cl | |
| $-CH_2-CH=CH_2$ | Cl | Cl | H | Cl | 169–171 |
| $-CH_2-CH=CHCl$ | Cl | Cl | H | Cl | 176–178* |
| $-CH_2-CH=CHBr$ | Cl | Cl | H | Cl | 163–169* |
| $-CH_2-\underset{Br}{\underset{\vert}{C}}=CH_2$ | Cl | Cl | H | Cl | |
| $-CH_2-CH=CH_2$ | Cl | Cl | H | F | 144–146 |
| $-CH_2-CH=CHCl$ | Cl | Cl | H | F | 164–165* |
| $-CH_2-CH=CHBr$ | Cl | Cl | H | F | 145–149,5* |
| $-CH_2-\underset{Br}{\underset{\vert}{C}}=CH_2$ | Cl | Cl | H | F | |
| $-CH_2-CH=CH_2$ | Cl | Cl | Cl | Cl | 175–177 |
| $-CH_2-CH=CHCl$ | Cl | Cl | Cl | Cl | 174–177* |
| $-CH_2-CH=CHBr$ | Cl | Cl | Cl | Cl | 188–191* |
| $-CH_2-\underset{Br}{\underset{\vert}{C}}=CH_2$ | Cl | Cl | Cl | Cl | |
| $-CH_2-CH=CH_2$ | Cl | Cl | Cl | F | 162–165 |
| $-CH_2-CH=CHCl$ | Cl | Cl | Cl | F | 163–165* |
| $-CH_2-CH=CHBr$ | Cl | Cl | Cl | F | 161–163* |
| $-CH_2-\underset{Br}{\underset{\vert}{C}}=CH_2$ | Cl | Cl | Cl | F | |
| $-CH_2-CH=CH_2$ | H | Cl | F | F | 158–161 |
| $-CH_2-CH=CHCl$ | H | Cl | H | Cl | 158–160* |
| $-CH_2-CH=CHCl$ | H | Cl | F | Cl | 142–146* |
| $-CH_2-CH=CHCl$ | H | Cl | Cl | Cl | * |
| $-CH_2-CH=CHCl$ | H | Cl | H | F | 148–150* |
| $-CH_2-CH=CHCl$ | H | Cl | Cl | F | * |
| $-CH_2-CH=CHCl$ | H | H | H | F | 149–152* |
| $-CH_2-CH=CHCl$ | H | H | H | Cl | 145–150* |
| $-CH_2-CH=CHCl$ | H | H | F | Cl | 142–144* |
| $-CH_2-CH=CHBr$ | Cl | H | F | Cl | 166–168* |
| $-CH_2-CH=CHBr$ | Cl | H | H | Cl | 124–125* |
| $-CH_2-CH=CHBr$ | Cl | H | H | F | 134–137* |
| $-CH_2-CH=CHBr$ | H | H | H | F | 128–132* |

-continued

| $R_1$ | $R_2$ | $R_3$ | $R_4$ | $R_5$ | Melting point [°C.] |
|---|---|---|---|---|---|
| $-CH_2-CH-CHBr$ | H | Cl | F | F | 170–172* |

*stereoisomeric mixture

EXAMPLE 2

Action against *Musca domestica*

A 50 g amount of freshly prepared CSMA nutrient medium for maggots was weighed off into each of a series of beakers. A specific amount of a 1% (by weight) acetonic solution of the respective active substance was transferred by pipette to the nutrient medium in each beaker. After a thorough mixing of the nutrient medium, the acetone was allowed to evaporate off for at least 20 hours. There were then deposited per active substance and concentration in each case 25 one-day-old *Musca domestica* maggots into each beaker containing the treated nutrient medium. After completion of pupation, the formed pupae were separated from the nutrient medium by flushing with water, and were placed into vessels closed with perforated lids. The pupae flushed out per batch were counted (toxic effect of the active substance on the development of the maggot), and then after 10 days the number of flies which had emerged from the pupae was determined.

Compounds according to the Example 1 exhibited a good action in the above test.

EXAMPLE 3

Action against *Lucilia sericata*

1 ml of an aqueous solution containing 0.5% of active substance was added to 9 ml of a culture medium at 50° C. About 30 freshly hatched *Lucilia sericata* larvae were then placed onto the culture medium, and after 48 and 96 hours, respectively, the insecticidal action was determined by ascertaining the mortality rate.

Compounds according to the Example 1 exhibited in this test a good action against *Lucilia sericata.*

EXAMPLE 4

Action against *Aedes aegypti*

Sufficient of a 0.1% acetonic solution of the respective active substance was transferred by pipette to the surface of 150 ml of water in a container to obtain conentrations of 10, 5 and 1 ppm in each case. After the acetone had evaporated off, 30–40 two-day-old Aëdes larvae were placed into each container. The mortality rate was ascertained after 1, 2 and 5 days.

Compounds according to Example 1 exhibited in this test a good action against *Aedes aegypti.*

EXAMPLE 5

Action against *Spodoptera littoralis* and *Heliothis virescens* (larvae; eating and contact action)

Potted cotton and soya-bean plants about 30 cm high were sprayed dripping wet with a diluted aqueous emulsion preparation of the active substance to be tested. After the drying of the applied coating, the cotton plants were each infested with 5 larvae in the third larval stage of Spodoptera, and the soya-bean plants each with 10 larvae in the third larval stage of Heliothis. The specimens were kept for 5 days under artificial light, at a temperature of about 26° C. with 50–60% relative humidity. The evaluation which followed was made on the basis of percentage mortality, reduction of eating, deformations, and inhibition of development, compared with corresponding results in the case of the untreated control specimens.

The compounds according to Example 1 exhibited high activity in this test.

EXAMPLE 6

Action against *Laspeyresia pomonella* (eggs)

Deposited *Laspeyresia pomonella* eggs, which were not older than 24 hours, were immersed on filter paper for 1 minute in an acetonic-aqueous solution containing 400 ppm of the active substance to be tested. After drying off the solution, the eggs were transferred to Petri dishes and kept at a temperature of 28° C. After 6 days, the pecentage rate of hatching from the treated eggs was determined.

Compounds according to Example 1 exhibited a good action in the above test.

EXAMPLE 7

Ovicidal action on *Spodoptera littoralis*

Eggs of *Spodoptera littoralis,* deposited on filter paper, were cut out of the paper and immersed in a 0.05% (by weight) solution of the active substance in an acetone/-water mixture (1:1). The deposited eggs treated in this manner were then taken out of the mixture, and placed at 21° C. with 60% relative humidity into plastic dishes. After 3 to 4 days, the hatching rate, that is to say, the number of larvae which had developed from the treated eggs, was determined.

Compounds according to Example 1 exhibited a good action in the above test.

EXAMPLE 8

Action against *Epilachna varivestis* (larvae)

*Phaseolus vulgaris* plants (bush beans) about 15–20 cm in height were sprayed with an aqueous emulsion preparation containing the active substance to be tested. After the drying of the sprayed-on coating, 10 larvae of *Epilachna varivestis* (Mexican bean beetle) in the 4th larval stage were settled onto each plant. A plastics cylinder covered with a copper-gauze lid was placed over the treated plants.

After 1 and 2 days, respectively, the acute action (% mortality) was determined. The test insects were observed for a further 3 days to effect an evaluation with respect to any damage from eating (antifeeding effect), and disturbances in development and in shedding.

Compounds according to Example 1 exhibited a good action in the above test.

EXAMPLE 9

Action against *Leptinotarsa decemlineata* (larvae)

15 cm tall potato plants in culture vessels were evenly sprayed until dripping wet, using a compressed-air sprayer, with an aqueous emulsion preparation containing the active substance to be tested at a concentration of 500 ppm. After the drying of the plants, that is to say, after about 1.5 hours, a plastics cylinder was placed over the plants, and onto each plant were settled 10 Colorado beetle larvae of the 3rd stage. The cylinders were then closed with a copper-gauze lid, and the specimens were left in darkness at 28° C. with 60% relative humidity.

After 1 and 2 hours, and also after 1, 2 and 8 days, respectively, an examination was made to determine mortality of the test insects (dorsal position) and the percentage damage caused by eating on the plants.

Compounds according to Example 1 exhibited a good action in the above test.

EXAMPLE 10

Chemosterilising action against *Anthonomus grandis*

Adult *Anthonomus grandis,* which had been hatched no longer than 24 hours, were transferred, in groups each of 25 beetles, to cages having lattice walls. The cages containing the beetles were then immersed for 5 to 10 seconds in an acetonic solution containing 1.0 percent by weight of the active substance to be tested. After the beetle were again dry, they were placed, for copulation and oviposition, into covered dishes containing feed. Deposited eggs were flushed out with running water two to three times weekly; they were counted, disinfected by being placed for two to three hours in an aqueous disinfectant (such as "Actamer B 100"), and then deposited into dishes containing a suitable larval diet. The eggs were examined after 7 days to determine whether larvae had developed from the deposited eggs.

In order to ascertain the duration of the chemosterilant effect of the active substances tested, the oviposition of the beetles was observed during a period of about four weeks. The evaluation was on the basis of the reduction of the number of eggs laid and larvae hatched in comparison with that of untreated control specimens.

Compounds according to Example 1 exhibited a good action in the above test.

What is claimed is:

1. A compound of the formula

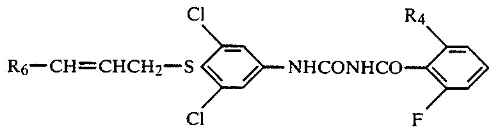

wherein $R_6$ is chloro or bromo and $R_4$ is hydrogen or fluoro.

2. The compound according to claim 1 of the formula

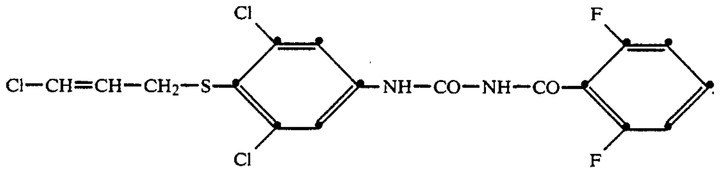

3. The compound according to claim 1 of the formula

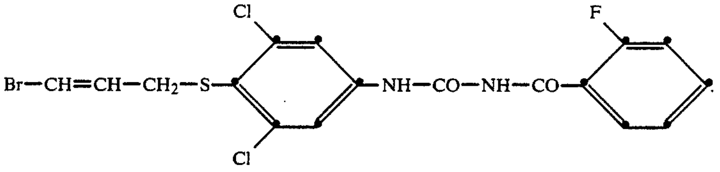

4. An insecticidal composition comprising (1) as active ingredient an insecticidally effective amount of a compound according to claim 1 and (2) a suitable carrier.

5. A method for combating insects which comprises applying to said insects or to a locus desired to be protected from said insects, an insecticidally effective amount of a compound according to claims 1, 2 or 3.

* * * * *